United States Patent [19]

Kobatake et al.

[11] Patent Number: 4,746,511
[45] Date of Patent: May 24, 1988

[54] LIPOPOLYSACCHARIDE AND PROCESS FOR PREPARATION THEREOF

[75] Inventors: Hiroshi Kobatake, Kyoto; Takahiro Suekane, Ibaragi; Kazuhiro Kumagai, Kyoto; Osamu Ohya, Nishinomiya, all of Japan

[73] Assignees: Chisato Maruyama; Zeria Shinyaku Kogyo Kabushiki Kaisha, both of Tokyo, Japan

[21] Appl. No.: 889,957

[22] Filed: Jul. 28, 1986

Related U.S. Application Data

[63] Continuation of Ser. No. 585,418, Mar. 2, 1984, abandoned.

[30] Foreign Application Priority Data

Mar. 4, 1983 [JP] Japan .................. 58-35621

[51] Int. Cl.⁴ .............. A61K 39/02; C12P 19/04; C12P 7/64; C07H 1/100
[52] U.S. Cl. .................. 424/92; 435/101; 435/134; 536/1.1
[58] Field of Search .............. 435/101, 134, 863, 843; 536/1.1; 424/88, 92

[56] References Cited

U.S. PATENT DOCUMENTS 4,315,919  2/1982  Shanbrom ............... 435/68 X
4,329,452  5/1982  Maruyama ............... 424/88 X
4,479,935 10/1984  Metianu et al. ............. 424/92

OTHER PUBLICATIONS

Gray et al. *Methods Enzymol* 35: 90–95, 1975.

*Primary Examiner*—Thomas G. Wiseman
*Assistant Examiner*—Richard C. Peet
*Attorney, Agent, or Firm*—Scrivener and Clarke

[57] ABSTRACT

A lipopolysaccharide characterized by a polysaccharide portion composed of D-arabinose and D-mannose in a 1:3/4 ration and 37 to 47% of a fatty acid portion having 14–19 carbon atoms bonded to the polysaccharide through an ester linkage. This lipopolysaccharide has physiological activities such as antitumor activity, immunizing activity, cell juvenescent activity, phagocyte activating activity, and infection preventing activity.

This lipopolysaccharide is prepared by culturing a Mycobacterium or a Propionibacterium and extracting the lipopolysaccharide from the culture with a non-ionic surface active agent and purifying the extract with a molecular sieve.

12 Claims, No Drawings

LIPOPOLYSACCHARIDE AND PROCESS FOR PREPARATION THEREOF

This application is a continuation, of application Ser. No. 585,418, filed Mar. 2, 1984, abandoned.

BACKGROUND OF THE INVENTION

The present invention relates to a lipopolysaccharide and a process for the preparation thereof. More specifically, the present invention relates to a lipopolysaccharide having physiological activities such as anti-tumor activity, immunizing activity, cell juvenescent activity, phagocyte activating activity and infection preventing activity and a process for preparing efficiently this lipopolysaccharide from actinomycetes and related bacteria.

Bacteria, especially bovine tubercle bacillus, BCG cell body and anaerobic Corynebacterium cell body, have been used as anti-tumor agents or immunizing agents, and it has been shown that these bacteria are effective. However, they have apparently strong side effects.

Attempts have been made to find bacteria having high effectivity without side effects, and trials have been vigorously made to remove components causing side effects from effective cells and isolate and purify effective components.

Researches have been made on the activities of cell body components of bacteria belonging to the genera Mycobacterium, Propionibacterium, Nocardia, etc., and various components having physiological activities have been isolated and purified and trials have been made to prepare substances having higher activities by modifying these components. For example, a cell wall skeleton component (see, for example, Japanese Patent Application laid open to public under No. 28813/1979), muramyl dipeptide (see, for example, Japanese Patent Application laid open to public under No. 156812/1977), a modified product of said dipeptide (see, for example, Japanese Patent Application laid open to public under No. 98922/1978), a glycolipid containing a long-chain fatty acid (see Japanese Patent Application laid open to public under No. 28830/1979) and a hot water extract (see Japanese Patents published under Nos. 6393/1961 and 43842/1973) have been shown. Furthermore, there has recently been disclosed a lipopolysaccharide obtained by purifying a hot water extract of cell body of human tubercle bacillus and a synthetic lipopolysaccharide obtained by coupling this lipopolysaccharide with a fatty acid through an ester linkage (see Japanese Patent Application laid open to public under No. 8320/1981).

We have made researches with a view to developing effective components having immunizing activity, anti-tumor activity and cell juvenescent activity without side effects from bacteria such as *Mycobacterium tuberculosis* strain Aoyama B (a human tubercle bacillus), *Mycobacterium bovis* (a bovine tubercle bacillus) and *Propionibacterium acnes* (a nonpathogenic anaerobic bacillus). As the result, we have found that if a non-ionic surface active agent is used in an extraction treatment of cells of these bacteria, substances causing side effects can be separated very easily without complicated operations such as those adopted in the conventional processes and a lipopolysaccharide having high anti-tumor activity, high immunizing activity and other physiological activities can be obtained efficiently. We have now completed the present invention based on this finding.

DETAILED DESCRIPTION OF THE INVENTION

The process for the preparation of a lipopolysaccharide according to the present invention will now be described.

Cell body obtained by culturing actinomyces or a related bacterium in an appropriate culture medium aerobically or anaerobically are collected by filtration using a cell-removing filter or by centrifugal separation and the collected cells are re-suspended in distilled water. The suspension is sterilized by heating and the dead cells are collected again by filtration or centrifugal separation. The collected dead cells are stirred in an aqueous solution of a non-ionic surface active agent such as Triton X-100 (polyoxyethylene tert-octyl-phenyl-ether) at room temperature and an extract is obtained by filtration or centrifugal separation. An appropriate organic solvent is added to the extract to precipitate a crude polysaccharide. The obtained crude polysaccharide is dissolved in an aqueous solution of a non-ionic surface active agent such as Triton X-100 (polyoxyethylene tert-octyl-phenyl-ether), the solution is passed through a column of an appropriate anion exchange resin to remove acidic components by adsorption, and a fraction of a lipopolysaccharide as a high-molecular weight substance is recovered by a molecular sieve column such as Bio-Gel A-5m. The recovered fraction is dialyzed by a dialysis membrane, the internal liquid is treated with α-amylase, amylo-glucosidase or proteinase and heated to precipitate the enzyme and the supernatant is dialyzed, desalted and freeze-dried to obtain a lipopolysaccharide.

Any of microorganisms classified as "Part 17, Actiomycetes and Related Organisms" in Bergey's Manual, new edition (1974), can be used as the starting bacterium in the present invention. These microorganisms are as follows: *Corynebacterium diphtheriae; Corynebacterium pseudotuberculosis; Corynebacterium xerosis; Corynebacterium renale; Corynebacterium kutscheri; Corynebacterium pseudodiphtheriticum; Corynebacterium equi; Corynebacterium bovis; Corynebacterium paurometabolum; Corynebacterium pyogenes; Corynebacterium enzymicum; Corynebacterium hoagii; Corynebacterium striatum; Corynebacterium murisepticum; Corynebacterium nephridii; Corynebacterium phocae; Corynebacterium vaginalis; Microbacterium flavum; Corynebacterium fascians; Corynebacterium rathayi; Corynebacterium agropyri; Corynebacterium tritici; Corynebacterium iranicum; Corynebacterium sepedonicum; Corynebacterium beticola; Corynebacterium ilicis; Corynebacterium humiferum; Corynebacterium humuli; Corynebacterium hypertrophicans; Corynebacterium acetoacidophilum; Corynebacterium acetophilum; Corynebacterium aurantiacum; Corynbacterium callunae; Corynebacterium citreum-mobilis; Corynebacterium ethanolaminophilum; Corynebacterium flaccumfaciens; Corynebacterium glutamicum; Corynebacterium herculis; Corynebacterium hydrocarboclastus; Corynebacterium lilium; Corynebacterium luteum; Corynebacterium mediolanum; Corynebacterium melassecola; Corynebacterium mycetoides; Corynebacterium nubilum; Corynebacterium roseum; Corynebacterium sanguinis; Arthrobacter globiformis; Arthrobacter simplex; Arthrobacter tumescens; Arthrobacter citreus; Arthrobacter terregens; Arthrobacter flavescens; Arthrobacter duodecadis; Arthrobacter luteus; Arthrobacter* marinus; Arthrobacter variabilis; Arthrobacter viscosus; Arthrobacter polychromogenes; Arthrobacter consociatus; Arthrobacter nicotinovorus; Brevibacterium linens; Brevibacterium acetylicum; Brevibacterium erythrogenes; Brevibacterium healii; Brevibacterium lipolyticum; Brevibacterium brunneum; Brevibacterium fulvum; Brevibacterium fuscum; Brevibacterium helvolum; Brevibacterium immotum; Brevibacterium marinopiscum; Brevibacterium sociovivum; Brevibacterium stationis; Brevibacterium maris; Brevibacterium imperiale; Brevibacterium incertum; Brevibacterium insectiphilium; Brevibacterium minutiferula; Brevibacterium quale; Brevibacterium tegumenticola; Brevibacterium ammoniagenes; Brevibacterium sulfureum; Brevibacterium protophormiae; Brevibacterium saperdae; Brevibacterium flavum; Brevibacterium immariophilum; Brevibacterium lactofermentum; Brevibacterium roseum; Brevibacterium saccharolyticum; Brevibacterium divaricatum; Brevibacterium leucinophagum; Brevibacterium liquefaciens; Brevibacterium pentosoalanicum; Brevibacterium pentoso-aminoacidicum; Brevibacterium lyticum; Brevibacterium albidum; Brevibacterium citreum; Brevibacterium luteum; Brevibacterium testaceum; Brevibacterium pusillum; Brevibacterium alanicum; Brevibacterium aminogenes; Brevibacterium chromogenes; Brevibacterium frigoritolerans; Brevibacterium halotolerans; Brevibacterium fermentans; Brevibacterium oxydans; Microbacterium lacticum; Microbacterium liquefaciens; Microbacterium flavum; Microbacterium thermosphactum; Cellulomonas flavigena; Cellulomonas acidula; Cellulomonas aurogena; Cellulomonas galba; Cellulomonas pusilla; Kurthia zopfii, Kurthia variabilis; Kurthia bessonii; Propionibacterium freudenreichii; Propionibacterium thoenii; Propionibacterium acidi-propionici; Propionibacterium jensenii; Propionibacterium avidum; Propionibacterium acnes; Propionibacterium lymphophilum; Propionibacterium granulosum; Eucobacterium foedans; Eucobacterium alactolyticum; Eucobacterium rectale; Eucobacterium limosum; Eucobacterium ruminantium; Eucobacterium saburreum; Eucobacterium budayi; Eucobacterium nitritogenes; Eucobacterium ventriosum; Eucobacterium mutiforme; Eucobacterium cylindroides; Eucobacterium moniliforme; Eucobacterium tortuosum; Eucobacterium cellulosolvens; Eucobacterium combesii; Eucobacterium tenue; Eucobacterium fissicatena; Eucobacterium contortum; Eucobacterium aerofaciens; Eucobacterium lentum; Eucobacterium endocarditidis; Eucobacterium helminthoides; Eucobacterium pseudotortuosum; Eucobacterium obstii; Eucobacterium ethylicum; Eucobacterium helwigiae; Eucobacterium ureolyticum; Eucobacterium parvum; Actinomyces bovis; Actinomyces odontolyticus; Actinomyces israelii; Actinomyces naeslundii; Actinomyces viscosus; Actinomyces eriksonii; Actinomyces humiferus; Actinomyces suis; Arachnia propionica; Bifidobacterium bifidum; Bifidobacterium adolescentis; Bifidobacterium infantis; Bifidobacterium breve; Bifidobacterium longum; Bifidobacterium pseudolongum; Bifidobacterium thermophilum; Bifidobacterium suis; Bifidobacterium asteroides; Bifidobacterium indicum; Bifidobacterium coryneforme; Bacterionema matruchotii; Rothia dentocariosa; Mycobacterium tuberculosis; Mycobacterium microti; Mycobacterium bovis; Mycobacterium africanum; Mycobacterium kansasii; Mycobacterium marinum; Mycobacterium simiae; Mycobacterium gastri; Mycobacterium nonchromogenicum; Mycobacterium terrae; Mycobacterium triviale; Mycobacterium gordonae; Mycobacterium scrofulaceum; Mycobacterium paraffinicum; Mycobacterium intracellulare; Mycobacterium avium; Mycobacterium xenopi; Mycobacterium ulcerans; Mycobacterium phlei; Mycobacterium vaccae; Mycobacterium diernhoferi; Mycobacterium smegmatis; Mycobacterium thamnopheos; Mycobacterium flavescens; Mycobacterium fortuitum; Mycobacterium peregrinum; Mycobacterium chelonei; Mycobacterium paratuberculosis; Mycobacterium leprae; Mycobacterium lepraemurium; Frankia alni; Frankia elaeagni; Frankia discariae; Frankia ceanothi; Frankia coriariae; Frankia dryadis; Frankia purshiae; Frankia cercocarpi; Frankia brunchorstii; Frankia casuarinae; Actinoplanes philippinensis; Actinoplanes armeniacus; Actinoplanes missouriensis; Actinoplanes utahensis; Spirillospora albida; Streptosporangium roseum; Streptosporangium vulgare; Streptosporangium amethystogenes; Streptosporangium pseudovulgare; Streptosporangium nondiastaticum; Streptosporangium longisporum; Streptosporangium viridogriseum; Streptosporangium album; Streptosporangium albidum; Streptosporangium viridialbum; Streptosporangium rubrum; Amorphosphorangium auranticolor; Ampullariella regularis; Ampullariella campanulata; Ampullariella lobata; Ampullariella digitata; Pilimelia terevasa; Pilimelia anulata; Planomonospora parontospora; Planomonospora venezuelensis; Planobispora longispora; Planobispora rosea; Dactylosporangium aurantiacum; Dactylosporangium thailandense; Dermatophilus congolensis; Geodermatophilus obscurus; Nocardia farcinica; Nocardia otitidus-caviarum; Nocardia brasiliensis; Nocardia asteroides; Nocardia transvalensis; Nocardia formicae; Nocardia coeliaca; Nocardia polychromogenes; Nocardia paraffinae; Nocardia petroleophila; Nocardia saturnea; Nocardia kuroishii; Nocardia rugosa; Nocardia rhodnii; Nocardia vaccinii; Nocardia minima; Nocardia blackwellii; Nocardia convoluta; Nocardia cellulans; Nocardia lutea; Nocardia globerula; Nocardia rubropertincta; Nocardia corallina; Nocardia salmonicolor; Nocardia rubra; Nocardia opaca; Nocardia calcarea; Nocardia restricta; Nocardia erythropolis; Nocardia marina; Nocardia atlantica; Nocardia aerocolonigenes; Nocardia aurantia; Nocardia butanica; Nocardia dassonvillei; Nocardia histidans; Nocardia madurae; Nocardia neoopaca; Nocardia pellegrino; Nocardia pelletieri; Nocardia sylvodorifera; Nocardia turbata; Nocardia tenuis; Nocardia variabilis; Pseudonocardia thermophila; Pseudonocardia spinosa; Streptomyces albolongus; Streptomyces viridaris; Streptomyces albo-niger; Streptomyces albosporeus; Streptomyces albovinaceus; Streptomyces aureocirculatus; Streptomyces baarnensis; Streptomyces clavifer; Streptomyces galtieri; Streptomyces bobili; Streptomyces longispororuber; Streptomyces longisporus; Streptomyces herbeus; Streptomyces albofaciens; Streptomyces albus; Streptomyces albus subsp. bruneomycini; Streptomyces albus subsp. pathocidicus; Streptomyces almquistii; Streptomyces aminophilus; Streptomyces cacaoi; Streptomyces chrestomyceticus; Streptomyces flocculus; Streptomyces gibsonii; Streptomyces herbescens; Streptomyces iodoformicus; Streptomyces ochraceiscleroticus; Streptomyces rangoon; Streptomyces rimosus; Streptomyces rimosus subsp. paromomycinus; Streptomyces rimosus subsp. pseudoverticillatus; Streptomyces spiroverticillatus; Streptomyces subflavus; Streptomyces varsoviensis; Streptomyces xantholiticus; Streptomyces albus subsp. fungatus; Streptomyces hydrogenans; Streptomyces vendargus; Streptomyces achromogenes; Streptomyces antibioticus; Streptomyces bikiniensis; Streptomyces cacaoi subsp. asoensis; Streptomyces cinereoruber; Streptomyces cinereoruber subsp. fructofermentans; Streptomyces cylindrosporus subsp. piceus; Streptomyces ederensis; Streptomyces fulvoviolaceus; Streptomyces fulvoviridis; Streptomyces gardneri; Streptomyces globosus; Strepto-

*myces griseorubiginosus; Streptomyces herbaricolor; Streptomyces indigoferus; Streptomyces litmocidini; Streptomyces narbonensis; Streptomyces nashvillensis; Streptomyces noboritoensis; Streptomyces phaeopurpureus; Streptomyces purpeofuscus; Streptomyces showdoensis; Streptomyces tanashiensis; Streptomyces violaceorectus; Streptomyces zaomyceticus; Streptomyces aburaviensis; Streptomyces caeruleus; Streptomyces catenulae; Streptomyces chrysomallus* subsp. *fumigatus; Streptomyces xanthocidicus; Streptomyces achromogenes* subsp. *rubradiris; Streptomyces anandii; Streptomyces aurantiogriseus; Streptomyces bobili* subsp. *sporificans; Streptomyces cinerochromogenes; Streptomyces cirratus; Streptomyces collinensis; Streptomyces eurythermus; Streptomyces galbus; Streptomyces galilaeus; Streptomyces griseoruber; Streptomyces griseosporeus; Streptomyces hygroscopicus* subsp. *ossamyceticus; Streptomyces kurssanovii; Streptomyces luteogriseus; Streptomyces massasporeus; Streptomyces mirabilis; Streptomyces multispiralis; Streptomyces naganishii; Streptomyces neyagawaensis; Streptomyces nojiriensis; Streptomyces olivochromogenes; Streptomyces phaeofaciens; Streptomyces pulveraceus; Streptomyces rameus; Streptomyces resistomycificus; Streptomyces rishiriensis; Streptomyces thermoviolaceus; Streptomyces violaceochromogenes; Streptomyces afghaniensis; Streptomyces arenae; Streptomyces attrocyaneus; Streptomyces chromofuscus; Streptomyces durhamensis; Streptomyces echinatus; Streptomyces filipinensis; Streptomyces fimbriatus; Streptomyces griseochromogenes; Streptomyces iakyrus; Streptomyces lucensis; Streptomyces malachitofuscus; Streptomyces malachitorectus; Streptomyces pilosus; Streptomyces albidofuscus; Streptomyces albogriseolus; Streptomyces ambofaciens; Streptomyces anthocyanicus; Streptomyces antimycoticus; Streptomyces argenteolus; Streptomyces atratus; Streptomyces aureofaciens; Streptomyces avellaneus; Streptomyces caesius; Streptomyces carnosus; Streptomyces chibaensis; Streptomyces coelescens; Streptomyces coelicolor* subsp. *achrous; Streptomyces coelicolor* subsp. *coelicofers; Streptomyces coelicolor* subsp. *coelicolatus; Streptomyces coelicolor* subsp. *coelicovarians; Streptomyces corchorusii; Streptomyces cyanogenus; Streptomyces diastaticus* subsp. *ardesiacus; Streptomyces diastatochromogenes* subsp. *bracus; Streptomyces endus; Streptomyces erumpens; Streptomyces griseoaurantiacus; Streptomyces griseofuscus; Streptomyces griseolosuffuscus; Streptomyces griseoluteus; Streptomyces griseus* subsp. *difficilis; Streptomyces humidus; Streptomyces hygroscopicus; Streptomyces hygroscopicus* subsp. *angustmyceticus; Streptomyces hygroscopicus* subsp. *decoyicus; Streptomyces hygroscopius* subsp. *glebosus; Streptomyces libani; Streptomyces libani* subsp. *rufus; Streptomyces lividans; Streptomyces lusitanus; Streptomyces lydicus; Streptomyces melanosporofaciens; Streptomyces misionensis; Streptomyces murinus; Streptomyces mutabilis; Streptomyces nigrescens; Streptomyces nodosus; Streptomyces nogalater; Streptomyces olivaceiscleroticus; Streptomyces olivaceoviridis; Streptomyces olivaceus; Streptomyces parvullus; Streptomyces platensis; Streptomyces plicatus; Streptomyces poonensis; Streptomyces psammoticus; Streptomyces purpurogeneiscleroticus; Streptomyces recifensis; Streptomyces rochei; Streptomyces rokugoensis; Streptomyces roseodiastaticus; Streptomyces rutgersensis* subsp. *castelarense; Streptomyces sayamaensis; Streptomyces sendaiensis; Streptomyces sioyaensis; Streptomyces tendae; Streptomyces thermovulgaris; Streptomyces tricolor; Streptomyces tubercidicus; Streptomyces tumemacerans; Streptomyces vastus; Streptomyces violaceolatus; Streptomyces violaceus-niger; Streptomyces violaceus-ruber; Streptomyces viridifaciens; Streptomyces atroolivaceus; Streptomyces cyanocolor; Streptomyces graminofaciens; Streptomyces griseoplanus; Streptomyces albaduncus; Streptomyces albospinus; Streptomyces albulus; Streptomyces althioticus; Streptomyces arabicus; Streptomyces atroolivaceus* subsp. *mutomycini; Streptomyces canus; Streptomyces chattanoogensis; Streptomyces chlorobiens; Streptomyces cuspidosporus; Streptomyces gancidicus; Streptomyces griseoflavus; Streptomyces griseoincarnatus; Streptomyces griseorubens; Streptomyces macrosporeus; Streptomyces malachiticus; Streptomyces matensis; Strepomyces noursei; Streptomyces olivoviridis; Streptomyces pseudogriseolus; Streptomyces rubiginosus; Streptomyces sparsogenes; Streptomyces viridiviolaceus; Streptomyces virido-diastaticus; Streptomyces calvus; Streptomyces cyanoalbus; Streptomyces finlayi; Streptomyces flaveolus; Streptomyces geysiriensis; Streptomyces herbiferis; Streptomyces pactum; Streptomyces akitaensis; Streptomyces akiyoshiensis; Streptomyces alanosinicus; Streptomyces albidus* subsp. *invertens; Streptomyces albochromogenes; Streptomyces ansochromogenes; Streptomyces ansochromogenes* subsp. *pallens; Streptomyces avidinii; Streptomyces carcinomycicus; Streptomyces castaneglobisporus; Streptomyces castaneus; Streptomyces cyanoflavus; Streptomyces djakartensis; Streptomyces erythrochromogenes* subsp. *narutoensis; Streptomyces glomerochromogenes; Streptomyces grisinus; Streptomyces haranomachiensis; Streptomyces hygrostaticus; Streptomyces insulatus; Streptomyces inversochromogenes; Streptomyces kitazuwaensis; Streptomyces mariensis; Streptomyces minutiscleroticus; Streptomyces mitakaensis; Streptomyces nigrogriseolus; Streptomyces ogaensis; Streptomyces piedadensis; Streptomyces regensis; Streptomyces robefuscus; Streptomyces robeus; Streptomyces robustrus; Streptomyces roseogriseolus; Streptomyces roseogriseus; Streptomyces sahachiroi; Streptomyces senoensis; Streptomyces tanashiensis* subsp. *cephalomyceticus; Streptomyces thermonitrificans; Streptomyces thermoviolaceus* subsp. *apingens; Streptomyces viridoniger; Streptomyces werraensis; Streptomyces alboflavus; Streptomyces bacillaris; Streptomyces cavourensis; Streptomyces cyaneofuscatus; Streptomyces fulvissimus; Streptomyces griseobrunneus; Streptomyces michiganensis; Streptomyces tsusimaensis; Streptomyces xanthochromogenus; Streptomyces albidoflavus; Streptomyces alboviridis; Streptomyces anulatus; Streptomyces badius; Streptomyces californicus; Streptomyces canescens; Streptomyces celluloflavus; Streptomyces cellulosae; Streptomyces champavatii; Streptomyces chrysomallus; Streptomyces citreofluorescens; Streptomyces coelicolor; Streptomyces felleus; Streptomyces fimicarius; Streptomyces floridae; Streptomyces fluorescens; Streptomyces globisporus; Streptomyces globisporus* subsp. *caucasicus; Streptomyces globisporus* subsp. *flavofuscus; Streptomyces globisporus* subsp. *vulgaris; Streptomyces gougerotii; Streptomyces griseinus; Streptomyces griseoloalbus; Streptomyces griseus; Streptomyces griseus* subsp. *alpha; Streptomyces griseus* subsp. *cretosus; Streptomyces griseus* subsp. *solvifaciens; Streptomyces intermedius; Streptomyces kanamyceticus; Streptomyces levoris; Streptomyces limosus; Streptomyces lipmanii; Streptomyces microflavus; Streptomyces odorifer; Streptomyces parvus; Streptomyces pluricolorescens; Streptomyces pneumonicus; Streptomyces praecox; Streptomyces puniceus; Streptomyces raffinosus; Streptomyces rutgersensis; Streptomyces sampsonii; Streptomyces setonii; Streptomyces sindenensis; Streptomyces sulphureus; Streptomyces willmorei; Streptomyces hawaiiensis; Streptomyces albohelvatus; Streptomyces aurigineus; Streptomyces canarius; Streptomyces chryseus; Streptomyces flavidovirens; Streptomyces helvaticus; Streptomyces*

*longisporoflavus; Streptomyces niveus; Streptomyces paucidiastaticus; Streptomyces spheroides; Streptomyces pimprina; Streptomyces capoamus; Streptomyces cinnabarinus; Streptomyces crystallinus; Streptomyces flavotricini; Streptomyces gobitricini; Streptomyces lincolnensis; Streptomyces melanogenes; Streptomyces phaeochromogenes; Streptomyces phaeochromogenes* subsp. *chloromyceticus; Streptomyces pseudovenezuelae; Streptomyces roseoviridis; Streptomyces spectabillis; Streptomyces subrutilus; Streptomyces umbrinus; Streptomyces venezuelae; Streptomyces xanthophaeus; Streptomyces aureomonopodiales; Streptomyces exfoliatus; Streptomyces filamentosus; Streptomyces prunicolor; Streptomyces roseofulvus; Streptomyces roseolus; Streptomyces roseoporus; Streptomyces rubiginosohelvolus; Streptomyces termitum; Streptomyces cinnamonensis; Streptomyces colombiensis; Streptomyces goshikiensis; Streptomyces katrae; Streptomyces lavendofoliae; Streptomyces lavendulae; Streptomyces lavendulae* subsp. *avireus; Streptomyces lavendulae* subsp. *brasilicus; Streptomyces lavendulae* subsp. *grasserius; Streptomyces lavendulcolor; Streptomyces luridus; Streptomyces orchidaceus; Streptomyces racemochromogenes; Streptomyces syringae; Streptomyces toxytricini; Streptomyces tuirus; Streptomyces vinaceus; Streptomyces virginiae; Streptomyces lateritus; Streptomyces flavovariabilis; Streptomyces janthinus; Streptomyces purpurascens; Streptomyces roseospinus; Streptomyces roseoviolaceus; Streptomyces violaceus; Streptomyces violaceus* subsp. *confinus; Streptomyces violaceus* subsp. *vicinus; Streptomyces violarus; Streptomyces violatus; Streptomyces yokosukanensis; Streptomyces albosporeus; Streptomyces aurantiacus; Streptomyces aureoverticillatus; Streptomyces aurini; Streptomyces cremeus; Streptomyces daghestanicus; Streptomyces fradiae; Streptomyces fragilis; Streptomyces fumanus; Streptomyces glomeroaurantiacus; Streptomyces griseoviridis; Streptomyces niveoruber; Streptomyces peucetius; Streptomyces phaeoviridis; Streptomyces roseiscleroticus; Streptomyces roseoflavus; Streptomyces roseolilacinus; Streptomyces rubo-cyaneus; Streptomyces tauricus; Streptomyces vinaceus-drappus; Streptomyces virocidus; Streptomyces erythraeus; Streptomyces luteofluorescens; Streptomyces erythrogriseus; Streptomyces garyphalus; Streptomyces lavendularectus; Streptomyces nagasakiensis; Streptomyces rubrolavendulae; Streptomyces cinnamonensis; Streptomyces ashchabadicus; Streptomyces polychromogenes; Streptomyces amakusaensis; Streptomyces caelestis; Streptomyces azureus; Streptomyces bellus; Streptomyces chartreusis; Streptomyces coeliatus; Streptomyces coerulatus; Streptomyces coerulatus* subsp. *amylolyticus; Streptomyces coeruleofuscus; Streptomyces coeruleorubidus; Streptomyces coerulescens; Streptomyces curacoi; Streptomyces cyaneus; Streptomyces cyanoglomerus; Streptomyces indigocolor; Streptomyces lanatus; Streptomyces lazureus; Streptomyces valynus; Streptomyces viridochromogenes; Streptomyces glaucescens; Streptomyces blensis; Streptomyces coerulatus* subsp. *anaseuli; Streptomyces coeruleoroseus; Streptomyces ipomoeae; Streptomyces spinosus; Streptomyces griseomycini; Streptomyces griseostramineus; Streptomyces prasinosporus; Streptomyces ghanaensis; Streptomyces hirsutus; Streptomyces prasinus; Streptomyces viridosporus; Streptomyces acrimycini; Streptomyces bambergiensis; Streptomyces prasinopilosus; Streptomyces horton; Streptomyces rectiviolaceus; Streptomyces lilacinofulvus; Streptomyces mauvecolor; Streptomyces violans; Streptomyces violascens; Streptoverticillium baldaccii; Streptoverticillium fervens; Streptoverticillium rubrochlorinum; Streptoverticillium biverticillatum; Streptoverticillium aureoversales; Streptoverticillium pentaticum; Streptoverticillium roseoverticillatum; Streptoverticillium rubroverticillatum; Streptoverticillium hiroshimense; Streptoverticillium salmonis; Streptoverticillium luteoverticillatum; Streptoverticillium olivoreticuli; Streptoverticillium waksmanii; Streptoverticillium griseocarneum; Streptoverticillium cinnamoneum; Streptoverticillium hachijoense; Streptoverticillium ardum; Streptoverticillium abikoense; Streptoverticillium albireticuli; Streptoverticillium eurocidicum; Streptoverticillium kishiwadense; Streptoverticillium mashuense; Streptoverticillium olivoverticillatum; Streptoverticillium orinoci; Streptoverticillium parvisporogenes; Streptoverticillium kentuckense; Streptoverticillium album; Streptoverticillium distallicum; Streptoverticillium ehimense; Streptoverticillium flavopersicum; Streptoverticillium griseoverticillatum; Streptoverticillium netropsis; Streptoverticillium rectiverticillatum; Streptoverticillium septatum; Streptoverticillium mobaraense; Streptoverticillium blastmyceticum; Streptoverticillium lavenduligriseum; Streptoverticillium lilacinum; Streptoverticillium kashmirense; Streptoverticillium thioluteum; Sporichthya polymorpha; Microellobosporia cinerea; Microellobosporia violacea; Microellobosporia flavea; Microellobosporia grisea; Micromonospora chalcea; Micromonospora halophytica; Micromonospora carbonacea; Micromonospora narashinoensis; Micromonospora melanosporea; Micromonospora echinospora; Micromonospora purpurea; Micromonospora purpureochromogenes; Micromonospora bicolor; Micromonospora coerulea; Micromonospora globosa; Micromonospora elongata; Micromonosora parva; Micromonospora gallica; Micromonospora acetoformici; Micromonospora propionici; Thermoactinomyces vulgaris; Thermoactinomyces sacchari; Actinobifida dichotomica; Actinobifida alba; Actinobifida chromogena; Thermomonospora curvata; Thermomonospora viridis; Microbispora rosea; Microbispora aerata; Microbispora amethystogenes; Microbispora bispora; Microbispora chromogenes; Microbispora diastatica; Microbispora parva; Microbispora thermodiastatica; Microbispora thermorosea; Micropolyspora brevicatena; Micropolyspora angiospora; Micropolyspora caesia; Micropolyspora faeni; Micropolyspora rectivirgula; Micropolyspora rubrobrunea; Micropolyspora thermovirida;* and *Micropolyspora viridinigra.* Cells used in the presetn invention may be those pulverized by a mechanical process using an ultrasonic wave generator or a French press, or cells which have been defatted by an organic solvent can also be used.

The lipopolysaccharide of the present invention is a white or greyish white powder. It is dissolved in distilled water or physiological saline solution to form a milky white solution but it is insoluble in an organic solvent. The lipopolysaccharide of the present invention comprises 53 to 63% of a polysaccharide containing D-arabinose and D-mannose as main constituent saccharides and 37 to 47% of a fatty acid having 14 to 19 carbon atoms which is coupled with the polysaccharide through an ester linkage. This lipopolysaccharide is thought to have a hydrophobic micelle structure and behaves as if it were a very high-molecular weight substance in various molecular weight measuring methods.

The lipopolysaccharide of the present invention can also be extracted by an aqueous solution of an alkali or an alkaline buffer solution.

The results of tests on physiological activities such as anti-tumor activity, cell juvenescent activity, antibody production enhancing activity and phagocyte activating activity will now be described in detail. In these tests, lipopolysaccharides prepared in Examples 1, 2 and 3 described hereinafter were used as sample substances, and physiological saline solution was used as a control according to the need.

The results of the anti-tumor activity test using the action of prolonging the life of a cancerous mouse as an index are described.

8-Weeks-old BALB/c male mice having body weight of 24.5±1.0 g were used as test animals and the peritoneal cavity of each mouse was inoculated with $1 \times 10^5$ cells of Meth A ascites tumor. The mice were divided into groups, each consisting of 10 mice. After the next day, the sample substance was administered to the peritoneal cavity once a day for 7 days. The T/C value was calculated from the mean survival date according to the following equation:

$$T/C\ (\%) = \frac{\text{mean survival date in administered group}}{\text{mean survival date in control group}} \times 100$$

In the control group, 0.2 ml of physiological saline solution was administered into the peritoneal cavity according to the same schedule as described above.

The test was terminated on the 60th day. The obtained results are shown in Table 1, from which it has been confirmed that the lipopolysaccharide of the present invention has a high life-prolonging effect to cancerous mice having the above-mentioned tumor.

The results of the anti-tumor effect test using the tumor propagation inhibiting effect as an index are described.

8-Weeks-old C57BL/6 female mice having body weight of 20.1±1.1 g were used as test animals, and each mouse was inoculated under the skin at the inguinal region with $1 \times 10^5$ cells of methylcholanthrene-induced tumor MC-1. The mice were divided into groups, each consisting of 10 mice. From the 10th day after the inoculation, the sample substance was administered in the peritoneal cavity once a day every four days. On the 21st day, the size (length × width, mm$^2$) of the tumor was measured by a dial caliper, and the tumor propagation inhibiting effect was evaluated based on the T/C value calculated according to the following equation:

$$T/C\ (\%) = \frac{\text{average tumor size in administered group}}{\text{average tumor size in control group}} \times 100$$

Each sample substance was sterilely administered as a solution in 0.2 ml of physiological saline solution. In the control group, physiological saline solution was administered in an amount of 0.2 ml per mouse according to the same schedule as described above.

The obtained results are shown in Table 2, from which it has been confirmed that the lipopolysaccharide of the present invention has a high propagation-inhibiting action to the above-mentioned tumor in mice.

TABLE 1

Anti-Tumor Activity by Prolongation of Life of Cancerous Mouse

| Sample Substance | Dose (μg/0.2 ml/mouse) | Number of Test Animals | Mean Survival Date ± S.E. | Number of Surviving Mice after 60 Days | T/C (%) |
|---|---|---|---|---|---|
| Control (physiological saline solution) | — | 10 | 27.1 ± 1.2 | 0 | 100 |
| Lipopolysaccharide of Example 1 | 100 | 10 | 50.2< | 4 | 185.2< |
| Lipopolysaccharide of Example 1 | 10 | 10 | 40.1< | 1 | 140.2< |
| Lipopolysaccharide of Example 1 | 1 | 10 | 32.8 ± 2.1* | 0 | 121.0 |
| Lipopolysaccharide of Example 2 | 100 | 10 | 44.7< | 2 | 164.9< |
| Lipopolysaccharide of Example 2 | 10 | 10 | 36.9 ± 2.0*** | 0 | 136.1 |
| Lipopolysaccharide of Example 2 | 1 | 10 | 29.7 ± 1.2 | 0 | 109.6 |
| Lipopolysaccharide of Example 3 | 100 | 10 | 49.8< | 4 | 183.8 |
| Lipopolysaccharide of Example 3 | 10 | 10 | 35.4 ± 1.9** | 0 | 130.6 |
| Lipopolysaccharide of Example 3 | 1 | 10 | 29.9 ± 1.8 | 0 | 110.3 |

*Student's t examination value, $p < 0.05$
**Student's t examination value, $p < 0.01$
***Student's t examination value, $p < 0.001$

TABLE 2

Anti-Tumor Activity by Inhibition of Propagation of Tumor

| Sample Substance | Dose (μg/0.2 ml/mouse) | Average Tumor Size ± S.E. (length × width, mm$^2$) | Number of Mice Surviving at Measurement | T/C (%) |
|---|---|---|---|---|
| Control (physiological saline solution) | — | 394.1 ± 18.6 | 9 | 100 |
| Lipopolysaccharide of Example 1 | 100 | 170.4 ± 31.7* | 10 | 43.2 |
| Lipopolysaccharide of Example 2 | 100 | 209.6 ± 19.8* | 10 | 53.2 |
| Lipopolysaccharide of Example 3 | 100 | 202.1 ± 21.4* | 10 | 51.3 |

*Student's t Examination value, $p < 0.001$

The results of the test of the cell juvenescent activity are now described.

Normal spleen cells of 8-weeks-old C57BL/6 female mouse were collected and cultured together with 100 μg of the lipopolysaccharide of Example 1, 2 or 3. The intake amount of $^3$H-thymidine by the cells was measured and the cell activating action of the lipopolysaccharide was evaluated. In the control, cells were cultured together with the corresponding amount of physiological saline solution. In each test group, the test was carried out by using cells collected from one animal, and the test was repeated on five animals.

The obtained test results are shown in Table 3, from which it has been confirmed that the lipopolysaccharide of the present invention prominently increases the intake amount of thymidine of mouse spleen cells and has cell activating and juvenescent actions.

TABLE 3

| Sample Substance | Cell Juvenescent Activity Intake Amount of $^3$H-thymidine (c.p.m.) |
|---|---|
| Control (physiological sline solution) | 8298 ± 201 |
| Lipopolysaccharide of Example 1 | 66139 ± 5379 |
| Lipopolysaccharide of Example 2 | 43271 ± 2110 |
| Lipopolysaccharide of Example 3 | 76045 ± 4998 |

The results of the antibody production enhancing activity test are now described.

The sample substance (100 μg) of Example 1, 2 or 3 was administered together with $10^8$ sheep red blood corpuscles (SRBC) in the tail vein of 8-weeks-old C57BL-6 female mouse (each group consisting of 5 mice) and the spleen was taken out after 4 days. The number of anti-SRBC plaque forming cells (PFC) was counted according to the method of Cunningham and Sjenberg and compared with that of the control group. The response index was calculated according to the following equation:

Response index (%) =

$$\frac{PFC \text{ number of administered group}}{PFC \text{ number of control group}} \times 100$$

The obtained results are shown in Table 4, from which it has been confirmed that the lipopolysaccharide of the present invention is a substance significantly enhancing the production of an antibody to SRBC and participating in the adjustment of immunity.

TABLE 4

| | Influences on Production of Antibody to Sheep Red Blood Corpuscles | |
|---|---|---|
| Sample Substance | Average PFC Number ± S.E. | Response Index (%) |
| Control | 189,700 ± 10,910 | 100 |
| Lipopolysaccharide of Example 1 | 478,800 ± 38,540 | 252 |
| Lipopolysaccharide of Example 2 | 428,600 ± 19,780 | 226 |
| Lipopolysaccharide of Example 3 | 399,400 ± 28,370 | 211 |

The results of the test of the phagocyte activating action are now described.

The sample substance obtained in Example 1, 2 or 3 was administered (100 μg in 0.2 ml of physiological saline solution) in the peritoneal cavity of 8-weeks-old BALB/c male mouse, and after 2 days, the peritoneal dropsy was taken out. Then, $10^3$ of tumor Meth A cells were added per $2 \times 10^4$ of cells adhering to a plastic dish in the peritoneal cells, and culturing was conducted for 24 hours in a bovine embryo serum-added medium. Then $^3$H-thymidine was added and culturing was continued for 16 hours. The action of the activated macrophage on the tumor cells was evaluated based on the intake amount of $^3$H-thymidine, and the macrophage activating activity of the sample substance was evaluated based on this action. The mice were divided into groups, each consisting of 10 mice, and in the control group, 0.2 ml of physiological saline solution was administered instead of the sample substance. The activating rate was caulculated according to the following equation:

activating rate (%) =

$$\frac{\left(\begin{array}{c}\text{average intake in}\\ \text{control group}\end{array}\right) - \left(\begin{array}{c}\text{average intake in}\\ \text{administered group}\end{array}\right)}{\text{average intake in control group}} \times 100$$

The obtained results are shown in Table 5, from which it has been confirmed that the lipopolysaccharide of the present invention is a substance promoting the activation of the mouse macrophage.

TABLE 5

| Effect of Inhibiting Propagation of Tumor Cells by Macrophage | |
|---|---|
| Sample Substance | Activating Rate (%) |
| Lipopolysaccharide of Example 1 | 82.6 |
| Lipopolysaccharide of Example 2 | 77.3 |
| Lipopolysaccharide of Example 3 | 89.4 |

When the lipopolysaccharide of the present invention was administered to the peritoneal cavities of C57BL/6 female mice and BALB/c male mice at dosages of 5 g/kg/day consecutively for 7 days, no change was caused in the test animals, and it has been found that the lipopolysaccharide of the present invention is very lowly toxic.

The lipopolysaccharide of the present invention is inherent to actinomycetes and related bacteria and comprises a polysaccharide containing D-arabinose and D-mannose as main constituent saccharides and a fatty acid composed mainly of palmitic acid and tuberculostearic acid which is coupled with the polysaccharide through an ester linkage. As is apparent from the foregoing test results, the lipopolysaccharide of the present invention is excellent in the anti-tumor effect, cell juvenescent effect, immunizing effect, etc., and this lipopolysaccharide is valuable in that it does not show side effects inherent to cells per se. Accordingly, it is expected that the lipopolysaccharide of the present invention will be used as an immunotherapeutic agent for tumors or an immunizing agent.

Furthermore, according to the process of the present invention, the above-mentioned lipopolysaccharide can be obtained efficiently by a simple operation using a nonionic surface active agent. Therefore, the process of the present invention is excellent as an industrial process.

The present invention will now be described in detail with reference to the following Examples that by no means limit the scope of the invention.

EXAMPLE 1

*Mycobacterium tuberculosis* strain Aoyama B was cultured in Sauton's medium for 5 weeks and cells were recovered by filtration, washed with water and suspended in distilled water. The suspension was heated and sterilized at 100° C. for 20 minutes. The dead cells were collected by filtration, washed with water and added to a 1.5% aqueous solution of Triton X-100 (polyoxyethylene tert-octyl-phenyl-ether) (about 5 times the weight of wet cells). The mixture was stirred at room temperature for 24 hours. Centrifugal separation was carried out under 20,000×g for 20 minutes, the supernatant was dialyzed by a dialysis membrane and ethyl alcohol was added to the internal liquid in an amount about 9 times the volume of the internal liquid. The mixture was stirred and centrifugal separation was carried out under 5,000×g for 10 minutes. The precipitate was collected and washed with ethyl alcohol and then with ethyl ether to obtain a crude lipopolysaccharide. This crude lipopolysaccharide was dissolved in a 50 mM solution of NaCl and the solution was charged in a molecular sieve column (for example, Bio-Gel A-5m equilibriated with a 50 mM solution of NaCl. Elution was effected with the same solution to collect a milky white fraction removed by the molecular sieve. The fraction was dialyzed in running water by using a dialysis membrane overnight and the internal liquid was treated with α-amylase and then with amyloglucosidase. The solution was dialyzed again, desalted and freeze-dried to obtain a lipopolysaccharide. The yield was about 0.1% based on the wet cells. From the results of the analysis, it was found that this substance was a lipopolysaccharide comprising 56% of a polysaccharide containing as constituent saccharides D-arabinose and D-mannose in a ratio of 1:4 and 44% of a fatty acid component composed mainly of saturated fatty acids having 16, 18 and 19 carbon atoms.

EXAMPLE 2

*Mycobacterium bovis* BCG was cultured in Sauton's medium for 4 weeks and obtained cells were washed with water, dried and defatted with ether-ethanol (1:1, v/v) and then with chloroform-methanol (1:1, v/v). Then, the cells were heated at 100° C. for 20 minutes in distilled water and recovered by filtration. The recovered cells were treated according to the same procedures as described in Example 1 to obtain a lipopolysaccharide. The yield was about 1% based on the dry cell. From the results of the analysis, it was found that the substance was a lipopolysaccharide comprising 59% of a polysaccharide containing as main constituent saccharides D-arabinose and D-mannose in a ratio of 1:4 and 41% of a fatty acid component composed mainly of saturated fatty acids having 16, 18 and 19 carbon atoms.

EXAMPLE 3

*Propionibacterium acnes* C-7 was anaerobically cultured in GAM broth medium for 4 days according to the stationary culturing method. Cells recovered by centrifugal separation were washed with physiological saline solution, pulverized by a French press and subjected to centrifugal separation. The pulverized cell was treated in the same manner as described in Example 1 to obtain a lipopolysaccharide. The yield was 0.2% based on the weight of the wet cells. From the results of the analysis, it was found that the lipopolysaccharide comprises 60% of a polysaccharide containing D-arabinose and D-mannose in a ratio of 1:3 and 40% of a fatty acid component composed mainly of fatty acids having 15 through 18 carbon atoms.

A culture of *Mycobacterium tuberculosis* strain Aoyama B has been deposited with the American Type Culture Collection, Rockville, Md., and added to its permanent collection as ATCC No. 31726.

A culture of *Mycobacterium bovis* strain BCG has been deposited with the American Type Culture Collection, Rockville, Md. and added to its permanent collection as ATCC No. 19015.

A culture of *Propionibacterium acnes* C-7 (collected and reserved in Fac. Med., Gifu Univ., Gifu, Japan) is the same culture that has been deposited in the American Type Culture Collection, Rockville, Md. as ATCC No. 11827.

What is claimed is:

1. A lipopolysaccharide isolated from a Mycobacterium or a Propionibacterium comprising 53 to 63% of a polysaccharide consisting of D-arabinose and D-mannose in the ratio of 1:3-4 and 37 to 47% of a fatty acid having 14–19 carbon atoms bonded to the polysaccharide through an ester linkage.

2. A process of reducing tumor activity comprising the administration of an effective amount of the lipopolysaccharide of claim 1.

3. A process of increasing antibody production comprising the administration of an effective amount of the lipopolysaccharide of claim 1.

4. A process of activating cells and causing juvenescent action comprising the administration of an effective amount of the lipopolysaccharide of claim 1.

5. A process of activating phagocyte action comprising the administration of an effective amount of the lipopolysaccharide of claim 1.

6. A pharmaceutical composition for administration to a patient which comprises a tumor reducing effective amount of the lipopolysaccharide of claim 1 and a pharmaceutically acceptable carrier.

7. A pharmaceutical composition for administration to a patient which comprises an antibody increasing effective amount of the lipopolysaccharide of claim 1 and a pharmaceutically acceptable carrier.

8. A pharmaceutical composition for administration to a patient which comprises a cell activating and juvenescent effective amount of the lipopolysaccharide of claim 1 and a pharmaceutically acceptable carrier.

9. A pharmaceutical composition for administration to a patient which comprises a phagocyte activating effective amount of the lipopolysaccharide of claim 1 and a pharmaceutically acceptable carrier.

10. A process for the preparation of a lipopolysaccharide which comprises the following steps:

(1) culturing bacterium belonging to the genus Mycobacterium in Sauton's medium for five weeks;

(2) collecting the cells produced by step (1) by filtration;

(3) washing the cells obtained by step (2) with water and re-suspending said cells in distilled water;

(4) sterilizing the suspension produced by step (3) at 100° C. for twenty minutes;

(5) collecting the dead cells produced by step (4) by filtration and washing said cells with water;

(6) adding the dead cells collected by step (5) to a 1.5% aqueous solution of polyoxyethylene tertoctyl-phenyl-ether about five times the weight of said dead cells and stirring the resulting mixture at room temperature for twenty-four hours;
(7) carrying out centrifugal separation of the mixture produced by step (6) under 20,000×g for twenty minutes;
(8) dialyzing the supernatant of step (7) by a dialysis membrane;
(9) adding ethyl alcohol to the internal liquid produced by step (8) in an amount nine times the volume of said internal liquid;
(10) stirring the product of step (9) and carrying out centrifugal separation under 5,000×g for ten minutes;
(11) collecting the precipitate of step (10), washing said precipitate with ethyl alcohol, and then with ethyl ether to obtain a crude lipopolysaccharide;
(12) dissolving the crude lipopolysaccharide of step (11) in a 50 mM solution of NaCl, charging the resulting solution to a molecular sieve column equilibrated with a 50 mM solution of NaCl, and eluting said column with a 50 mM solution of NaCl to collect a milky white fraction removed by said molecular sieve;
(13) dialyzing said milky white fraction of step (12) in running water by using a dialysis membrane overnight;
(14) treating the internal liquid produced by step (13) with α-amylase, and then with amyloglucosidase;
(15) dialyzing the product of step (14);
(16) desalting the product of step (15); and
(17) freeze-drying the product of step (16) so as to produce a lipopolysaccharide as claimed in claim 1.

11. A process for the preparation of a lipopolysaccharide which comprises the following steps:
(1) culturing bacterium belonging to the genus Mycobacterium in Sauton's medium for four weeks;
(2) collecting the cells produced by step (1) by filtration;
(3) washing the cells obtained by step (2) with water, drying and defatting said cells with ether-ethanol (1:1 v/v) and then with chloroform-methanol (1:1, v/v), and re-suspending said cells in distilled water;
(4) sterilizing the suspension produced by step (3) at 100° C. for twenty minutes;
(5) collecting the dead cells produced by step (4) by filtration and washing said cells with water;
(6) adding the dead cells collected by step (5) to a 1.5% aqueous solution of polyoxyethylene tert-octyl-phenyl-ether about five times the weight of said dead cells and stirring the resulting mixture at room temperature for twenty-four hours;
(7) carrying out centrifugal separation of the mixture produced by step (6) under 20,000×g for twenty minutes;
(8) dialyzing the supernatant of step (7) by a dialysis membrane;
(9) adding ethyl alcohol to the internal liquid produced by step (8) in an amount nine times the volume of said internal liquid;
(10) stirring the product of step (9) and carrying out centrifugal separation under 5,000×g for ten minutes;
(11) collecting the precipitate of step (10), washing said precipitate with ethyl alcohol, and then with ethyl ether to obtain a crude lipopolysaccharide;
(12) dissolving the crude lipopolysaccharide of step (11) in a 50 mM solution of NaCl, charging the resulting solution to a molecular sieve column equilibrated with a 50 mM solution of NaCl, and eluting said column with a 50 mM solution of NaCl to collect a milky white fraction removed by said molecular sieve;
(13) dialyzing said milky white fraction of step (12) in running water by using a dialysis membrane overnight;
(14) treating the internal liquid produced by step (13) with α-amylase, and then with amyloglucosidase;
(15) dialyzing the product of step (14);
(16) desalting the product of step (15); and
(17) freeze-drying the product of step (16) so as to produce a lipopolysaccharide as claimed in claim 1.

12. A process for the preparation of a lipopolysaccharide which comprises the following steps:
(1) culturing bacterium belonging to the genus Propionibacterium anaerobically in GAM broth medium for four days according to the stationary culturing method;
(2) collecting the cells produced by step (1) by centrifugal separation;
(3) washing the cells obtained by step (2) with physiological saline solution, pulverizing said cells with a French press and subjecting said pulverized cells to centrifugal separation;
(4) sterilizing the suspension produced by step (3) at 100° C. for twenty minutes;
(5) collecting the dead cells produced by step (4) by filtration and washing said cells with water;
(6) adding the dead cells collected by step (5) to a 1.5% aqueous solution of polyoxyethylene tert-octyl-phenyl-ether about five times the weight of said dead cells and stirring the resulting mixture at room temperature for twenty-four hours;
(7) carrying out centrifugal separation of the mixture produced by step (6) under 20,000×g for twenty minutes;
(8) dialyzing the supernatant of step (7) by a dialysis membrane;
(9) adding ethyl alcohol to the internal liquid produced by step (8) in an amount nine times the volume of said internal liquid;
(10) stirring the product of step (9) and carrying out centrifugal separation under 5,000×g for ten minutes;
(11) collecting the precipitate of step (10), washing said precipitate with ethyl alcohol, and then with ethyl ether to obtain a crude lipopolysaccharide;
(12) dissolving the crude lipopolysaccharide of step (11) in a 50 mM solution of NaCl, charging the resulting solution to a molecular sieve column equilibrated with a 50 mM solution of NaCl, and eluting said column with a 50 mM solution of NaCl to collect a milky white fraction removed by said molecular sieve;
(13) dialyzing said milky white fraction of step (12) in running water by using a dialysis membrane overnight;
(14) treating the internal liquid produced by step (13) with α-amylase, and then with amyloglucosidase;
(15) dialyzing the product of step (14);
(16) desalting the product of step (15); and
(17) freeze-drying the product of step (16) so as to produce a lipopolysaccharide as claimed in claim 1.

* * * * *